US010610150B2

(12) United States Patent
Berry

(10) Patent No.: US 10,610,150 B2
(45) Date of Patent: Apr. 7, 2020

(54) REMOTE MICROELECTROMECHANICAL LABOR DETECTION SYSTEM

(71) Applicant: Daniel K. Berry, Olathe, KS (US)

(72) Inventor: Daniel K. Berry, Olathe, KS (US)

( * ) Notice: Subject to any disclaimer, the term of this patent is extended or adjusted under 35 U.S.C. 154(b) by 128 days.

(21) Appl. No.: 14/706,202

(22) Filed: May 7, 2015

(65) Prior Publication Data
US 2016/0324459 A1 Nov. 10, 2016

(51) Int. Cl.
*A61B 5/00* (2006.01)
*H04B 7/155* (2006.01)
*H04L 29/08* (2006.01)
*A61B 5/145* (2006.01)

(52) U.S. Cl.
CPC .......... *A61B 5/435* (2013.01); *A61B 5/14539* (2013.01); *H04B 7/155* (2013.01); *H04L 67/12* (2013.01); *A61B 2560/0209* (2013.01); *A61B 2560/0214* (2013.01); *A61B 2562/028* (2013.01)

(58) Field of Classification Search
CPC ...................................................... A61B 5/435
See application file for complete search history.

(56) References Cited

U.S. PATENT DOCUMENTS

| 3,768,459 | A | * | 10/1973 | Cannon | A61B 5/435 324/207.17 |
|---|---|---|---|---|---|
| 5,406,961 | A | * | 4/1995 | Artal | A61B 5/1076 600/587 |
| 5,438,996 | A | * | 8/1995 | Kemper | A61B 5/1076 600/448 |
| 5,851,188 | A | * | 12/1998 | Bullard | A61B 5/1076 600/448 |
| 6,363,271 | B1 | * | 3/2002 | Berry | A61B 5/4294 600/304 |
| 6,383,137 | B1 | * | 5/2002 | Berry | A61B 5/1076 600/304 |
| 6,423,000 | B1 | * | 7/2002 | Berry | A61B 5/1076 600/304 |
| 8,100,840 | B2 | | 1/2012 | Berma | |
| 2009/0240168 | A1 | * | 9/2009 | Verma | A61B 5/435 600/588 |
| 2016/0310061 | A1 | * | 10/2016 | Campero | A61B 5/4343 |

* cited by examiner

*Primary Examiner* — Michael R Bloch
(74) *Attorney, Agent, or Firm* — Arthur K. Shaffer; Intellectual Property Center, LLC

(57) ABSTRACT

The present invention provides an improved light system for labor detection by monitoring the status of a cervix, including dilation, during pregnancy and for monitoring vaginal pH at the cervix to detect the leakage of amniotic fluid, including a MEMS receiver programmed to receive and process MEMS cervical data into cervical status data for transmission to a remote network monitor a first cervical MEMS device positioned at a first cervix location and a second cervical MEMS device positioned at a second cervix location providing MEMS cervical data for transmission to the short range wireless receiver for detecting labor.

9 Claims, 4 Drawing Sheets

REMOTE MICROELECTROMECHANICAL LABOR DETECTION SYSTEM

FIELD OF THE INVENTION

The present invention is broadly directed to labor detection systems and more specifically to a microelectromechanical labor detection system for detecting for the cervical dilation and pH status using a microelectromechanical implant device.

BACKGROUND OF THE INVENTION

The moment labor begins within a pregnant patient is sometimes difficult to detect because of several reasons including false labor or "Braxton Hicks contractions" which sometimes giving a patient the false sense of labor in contrast with actual labor. False labor contractions may be highly irregular and may be sensed in locations and with intensities unlike actual labor. However, false labor contractions may be very similar to actual labor. Some patients and caregivers may attribute these false labor contractions to actual labor or out of an abundance of caution may require the patient to travel to the hospital or other medical office to determine if actual labor has begun. It thus would be beneficial to provide for a remote labor monitoring system where the caregiver could detect and monitor actual labor without requiring that the patient visit a medical office.

Another factor that can make the detection of the onset of labor difficult is that in some cases the patient experiences silent labor, in which the onset of labor occurs without pronounced contractions and where dilation and effacement of the cervix are not accompanied with traditional contractions associated with common labor. For example, this may occur during normal pregnancy, premature birth conditions, and in spontaneous abortions (miscarriages). In some cases, contractions may not actually occur until minutes before actual delivery of the child at which point it may be too late to travel to a hospital or even to coordinate the necessary medical care. It therefore would be beneficial to identify the onset of labor, monitor the progress of labor, and to notify the patient and necessary caregiver prior to the onset of noticeable contractions. Identifying silent labor in time to transport the patient to a hospital would be beneficial in that it would reduce the number of maternal and fetal deaths that occur when delivery occurs outside of a hospital, or in cases where complications of births occur that require surgical intervention or specialized medical equipment. It would also be beneficial to alert the patient and caregiver of the initiation of a spontaneous abortion (miscarriage) in time to prevent it front occurring and thus save the life of the fetus.

In addition, in some instances, the bag of waters—or amniotic sac—which is a membrane filled with amniotic fluid that surrounds the fetus during pregnancy ruptures prior to the onset of labor, which may cause the amniotic fluid to leak through the cervix and the vagina requiring immediate medical attention. In some cases, this fluid leakage goes unnoticed because the release of fluid does not always occur as a sudden gush and may be a slow trickle resembling urinary leakage. When the membranes rupture, bacteria can enter through the rupture site. If the fetus is not delievered within 24 hours of the rupture, the bacteria may cause fetal demise (death). Knowledge of when the membranes have ruptured is important in order to induce labor in time to prevent fetal demise. Therefore, it would be beneficial to detect release of amniotic fluid and notify a caregiver of the release to coordinate travel to a medical office for medical care.

Once labor begins it may not occur in a linear fashion. Sometimes it can begin very gradually while in others, it can occur very rapidly. The active part of labor begins when the patient begins to push. However, to save energy, strength and to prevent unnecessary tears of the cervix, patients are not encouraged to push until the conclusion of the first stage of delivery which occurs when the cervix is dilated to approximately 10 cm. Generally, the patient is encouraged to seek medical attention only after the cervix is dilated 4 cm and the cervix is effaced and the membranes have ruptured. Pushing is generally encouraged when the cervix has achieved a maximum dilation of approximately 10 cm. Few patients can determine their dilation or the status of their cervix without medical supervision. In standard procedures, the measurement of the cervix involves the insertion of fingers or instruments into a women's vagina requiring additional medical resources and causing unnecessary discomfort to patients who are already uncomfortable. During labor, constant and repeated measurements of the cervix are required during the various stages of labor. Therefore, there is a need for a way to actively measure and monitor the cervix during the labor process which does not tax the already limited medical personnel to perform an otherwise routine measurement of the cervix while waiting for the birth to begin while the patient is not in active labor or the actual delivery is not eminent.

Many attempts to monitor the onset and condition of labor including U.S. Pat. Nos. 6,423,000, 6,383,137, 6,363,271, 5,807,281, 5,406,981, 3,768,459, 5,438,996, 4,476,871, 5,876,357, 5,713,371, 5,851,188, 4,719,925, 4,682,609, 4,207,902, 3,583,389, 4,203,450, 4,055,839, 4,264,900, 4,232,686, 5,776,073, 5,450,837 and 5,879,293 which all fail to teach the present invention which as further described and disclosed below provides a remote microelectromechanical labor monitoring system which provides a rapid and easy continuous measurement and monitoring of the cervix during pregnancy and labor to provide medical caregivers using a handheld remote monitoring device relevant medical data regarding the pregnancy and delivery of the child transmitted to the handheld remote monitoring in numeric and visual representations.

SUMMARY OF THE INVENTION

The present invention is an improved system for labor detection by monitoring the status of a cervix during pregnancy. The system comprising a MEMS receiver comprising a processor, a controller, a short range wireless receiver and a long range wireless transceiver, said controller coupled to said processor, said short range wireless receiver and said long range wireless transceiver, the MEMS receiver programmed to receive and process MEMS cervical data into cervical status data for transmission to a remote network monitor, a first cervical MEMS device having a biocompatible coating positioned at a first cervix location and comprising a first power supply coupled to a first proximity sensor; and a second cervical MEMS device having a biocompatible coating and positioned at a second cervix location is in communication with said first cervical MEMS device and comprising a transmitter, a MEMS processor, a second power supply coupled to a second proximity sensor, wherein said MEMS processor provides MEMS cervical data for transmission by said transmitter to said short range wireless receiver, said MEMS cervical data including distance data calculated by said MEMS processor between said first and said second proximity sensors wherein said distance data detects labor.

Various objects and advantages of the present invention will become apparent from the following description taken in conjunction with the accompanying drawings wherein are set forth, by way of illustration and example, certain embodiments of this invention. The drawings submitted herewith constitute a part of this specification, include exemplary embodiments of the present invention, and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
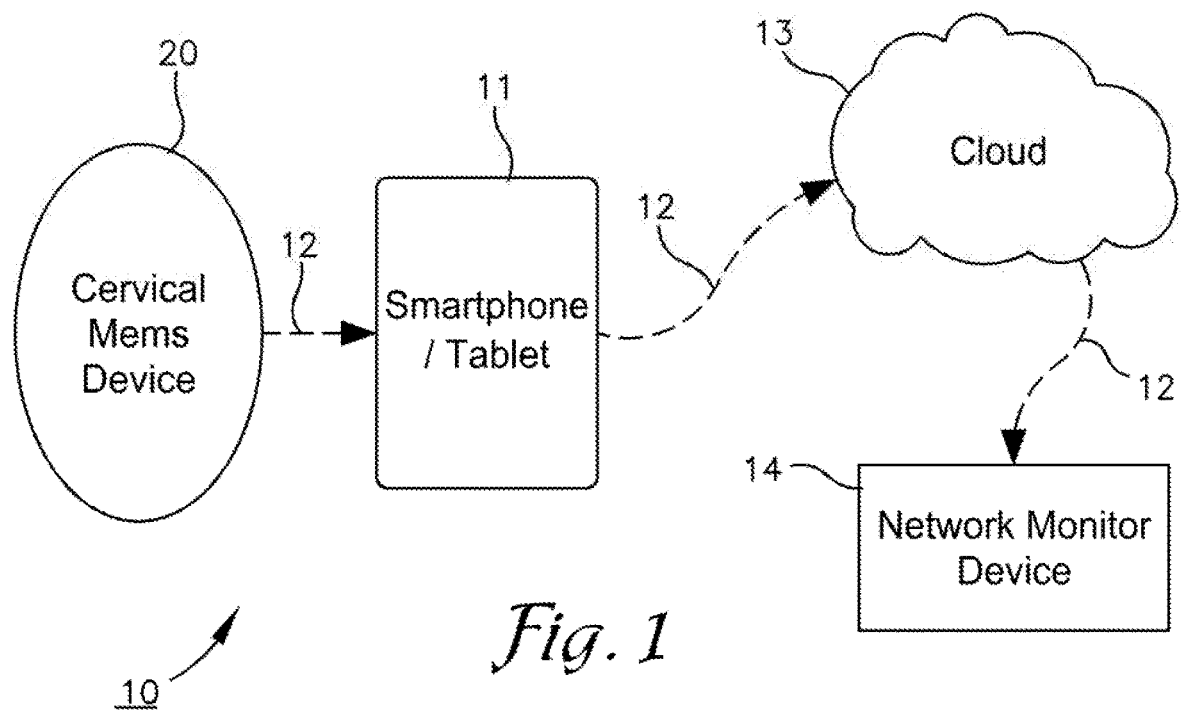
FIG. 1 is a system diagram of an embodiment of the present invention in an exemplary networked environment where a handheld device is in network communication with a network monitoring device for receiving medical data.

Referring to the drawings in more detail, the reference numeral 10 (FIGS. 1-2) generally designates an embodiment of a remote microelectromechanical labor detection system. The exemplary system diagram depicted in FIG. 1 in which systems or methods described herein may be implement may include a plurality of cervical MEMS receivers 11 which may be implemented on handheld portable communication devices such as smartphones, tablets, computers, or may include one or more content servers (not shown) in communication with a storage device (not shown) for retrievably storing medical data (not shown) transmitted by at least one cervical microelectromechanical implant 20 also referred to herein as a MEMS sensor or MEMS device which is adapted for implanting in association with a cervical site for use during pregnancy and in electronic communication with other networked computing device(s) including the various electronically connected devices connected via a electronic communications network 12 which may include communication through a remote network or cloud 13 to a remote network monitoring device 14. While FIG. 1 shows a particular number and arrangement of devices, in practice, the system 10 may include additional, fewer, different, or differently arranged devices than as shown in FIG. 1. For example, the receipt and storage of medical data (not shown) may be implemented using multiple, possibly distributed, networked computing devices 11 or they may be implemented within a single networked computing device 11 as illustrated.

Generally, a pair of MEMS sensors 20 are attached on opposite sides of a patient's cervix and cervix status data is collected from each MEMS sensor 20 and processed within a processor associated with at least one of the MEMS sensors 20. Cervix status data may include but is not limited to repeated or continuous measurements using digital, Doppler or sonographic means, pressures, temperatures, uterine, vaginal and cervix characteristics such as the dimensions, contractions and morphology; fluids such as blood, urine, amniotic and vaginal fluid composition characteristics such as pH, glucose, proteins, non-protein nitrogen compounds, carbohydrates, lipids, inorganic constituents; respiratory gases, cardiac output, arterial or venous $PO_2$, $O_2$, $CO_2$, time, uterine contraction monitoring including the frequency, duration and amplitude.

In general, the pair of cervical MEMS devices 20 measures changes in the cervix during pregnancy and collects the cervical status data and wirelessly transmits the data to the MEMS receiver. As further illustrated in FIG. 3, the pair of cervical MEMS devices 20 is positioned along the cervix 2 symmetrically along an axis (not shown) generally extending through the vaginal opening 7. Once processed, the MEMS cervical data may be stored in an integrated memory element or it may be transmitted to the MEMS receiver 11 for processing and storage within associated memory 11a.

Figure 2:
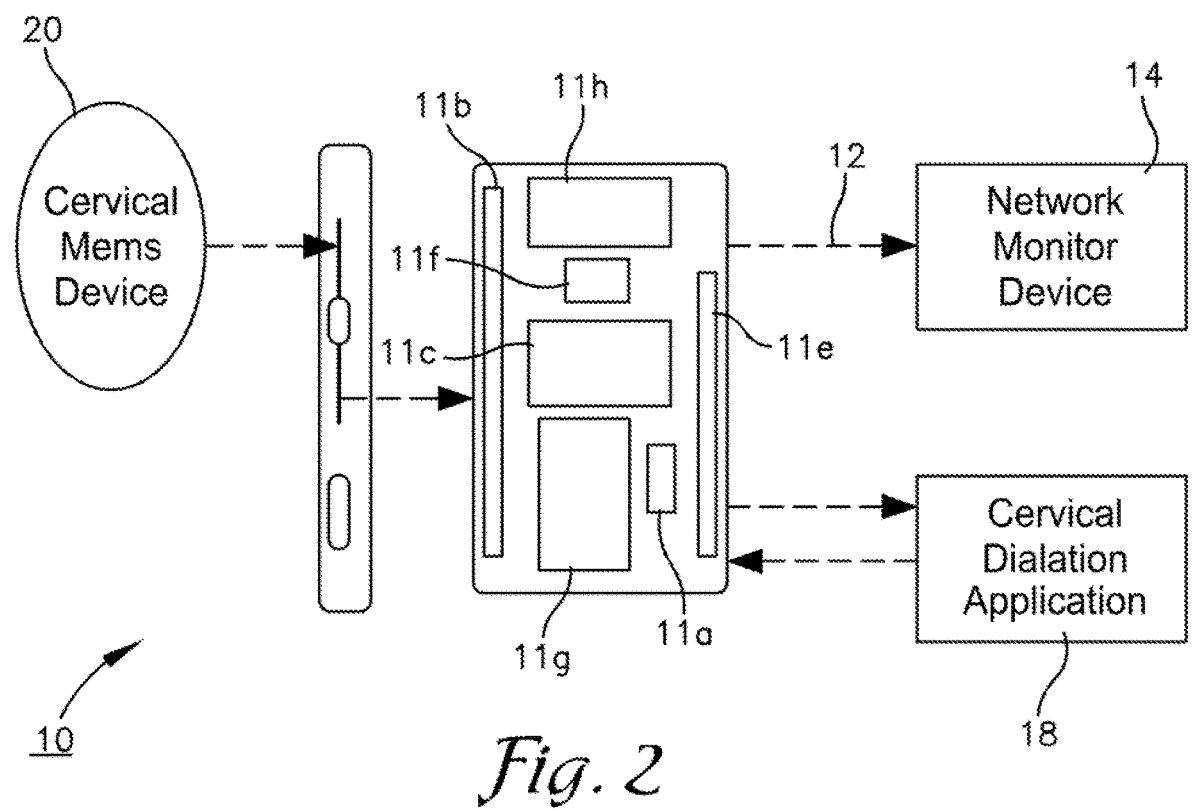
FIG. 2 is representative communication block diagram in accordance with an embodiment of the present invention, the remote microelectromechanical labor notification system.

FIG. 2 depicts one embodiment of the MEMS receiver 11 with an integrated receiver 11h coupled to a network monitoring device 14 via a wireless network 12. The integrated receiver 11h includes both a transmitting portion and a receiving portion for receiving MEMS cervical data from the MEMS devices 20 via the short range wireless receiver 11e and for transmitting cervical status data 23 processed by the processor 11f via the long range wireless transceiver 11b. The MEMS receiver 11 is generally a suitable wireless communication device such as a cellular phone, smartphone, PDA or tablet and may involve communication with a plurality of networks including a cellular telephone network for the receipt and transmission of cervix status data. The MEMS receiver includes a controller 11c for controlling the short range wireless receiver 11b and the long range wireless transmitter 11e and for receiving sensory data by the receiver 11h and for processing the received data by the processor 11f and if desired for storage within memory 11a. The controller 11c and the remaining integrated circuity is powered by the power supply 11g as needed.

In operation, the processes 11f determines the numerical values from the received sensory data and calculates the changes between readings which may for example correspond to a function of time which may be provided by an internal clocking circuitry. Based upon the numerical determination, the processor 11f can store the data individually within the memory device 11a or process it as cervical status data 23 for transmission by the long range wireless transceiver 11b as desired or as configured.

The network monitor device 14 generally is adapted for communication with a plurality of MEMS receivers 11 simultaneously collecting a plurality of cervix status data associated with each MEMS receiver 11, processing the received data, arranging and grouping the received plurality of data as desired. The MEMS receiver 11 also includes a power supply 11g such as a battery.

FIG. 2 is an exemplary block diagram of an embodiment of the invention, illustrating the MEMS receiver 11 in more detail than FIG. 1. One or more cervical MEMS device 20 may be communicably coupled to the cervical MEMS receiver 11. The coupling may be provided by via a short-range wireless system, such as Bluetooth transceivers. Alternatively, the coupling may be provided by wires or optical cable. The cervical MEMS receiver 11 includes memory 11a, short-range wireless receiver 11e in communication with at least one MEMS device 20, long-range wireless transceiver 11b in communication with network monitor device 14, and receiver 11h in selective communication with controller 11c through processor 11f. the Receiver 11h processes the received sensory data to form the cervical status data 23 which is associated with the communications transmitted from the long range wireless transceiver 11b through the wireless network such as a cellular telephone network, in which the transmission from the long range wireless transceiver 11b is received by a nearby cellular tower and then sent from tower to tower until it is received by a cellular data facility which then transmits the communication to the remote monitor device 14, for example. Power supply 11g provides any necessary power for the various circuity or electrical componentry. The long-range wireless transceiver 11b may be replaced by any suitable wireless transceiver, such as a Wi-Fi transceiver (not shown).

Controller 11c directs operation of the cervical MEMS receiver 11. The controller 11c may be implemented by a microprocessor executing instructions stored in a memory, such as the memory 11a or another memory. The controller 11c receives MEMS cervical data from the cervical MEMS device 20 and processes it as cervical status data 23 which is then stored in the memory 11c. The controller 11c may transmit the received data or a less detailed version of received data to the long-range wireless transceiver 11b for transmission, via the wireless network 12, to the remote network monitor 16 via the network monitor device 14. The controller 11c may be coupled to the long-range wireless transceiver 11b via wires, optical cables or a short-range wireless system, such as Bluetooth.

Optionally or alternatively, part or all of the functions of the controller 11c and the memory 11a may be implemented by a processor and a memory within the long-range wireless transceiver 11b. For example, a "smart phone" may store and execute an application program (cervical dilation application) 18 configured to receive the data from the cervical MEMS device 20, store the received, data in a memory of the cervical MEMS receiver 11 such as but, not limited to a smart phone and transmit a subset of the collected data to the remote network monitoring device 14. In response to a user activated request on the cervical MEMS receiver 11 or from a remote network monitoring device 14, the cervical dilation application 18 may cause the controller 11c to fetch MEMS cervical data and process it as cervical status data 23 and then transmitting the cervical status data 23 or a selected subset of the cervical status data 23 to the cervical dilation application 18 or the remote network monitoring device 14. Furthermore, the cervical dilation application 18 may alter, such as in response to commands to the cervical MEMS receivers 11 from the remote network monitoring device 14, data collection parameters, such as data acquisition frequency, data transmission frequency, transmitted or received data.

In operation, the controller 11c and the long-range wireless transceiver 11b such as but not limited to a cellular antenna may establish a connection through standard authenticity and verification procedures based in part on the selected communication protocol. The cervical MEMS receiver 11 generally receives plural MEMS cervical data also referred to herein as sensory data from the MEMS devices 20, processes the collected MEMS cervical data as desired and selectively transmits cervical status data 23 which is processed from the collected MEMS cervical data to a remote network monitoring device 14. The MEMS receiver 11 may be implemented as one physical assembly or may be implemented as two physically separable components, such as but not limited to one component including the controller 11c and the memory 11a, and the other component including the long-range wireless transceiver 11b. In such a case, the two components may communicate with each other via a short-range wireless system, such as Bluetooth (not shown). In operation, the system may include the steps of receiving the MEMS cervical data from the cervical MEMS device 20 using a short range wireless receiver (MEMS antenna) 11e located association with the MEMS receiver 11, collecting, processing and storing plural MEMS cervical data in memory 11a by the processor 11f, and transmitting the processed cervical status data 23 or a subset thereof between the MEMS receiver 11 and the remote network monitoring device 14 with the long range wireless transceiver 11b.

Figure 3:
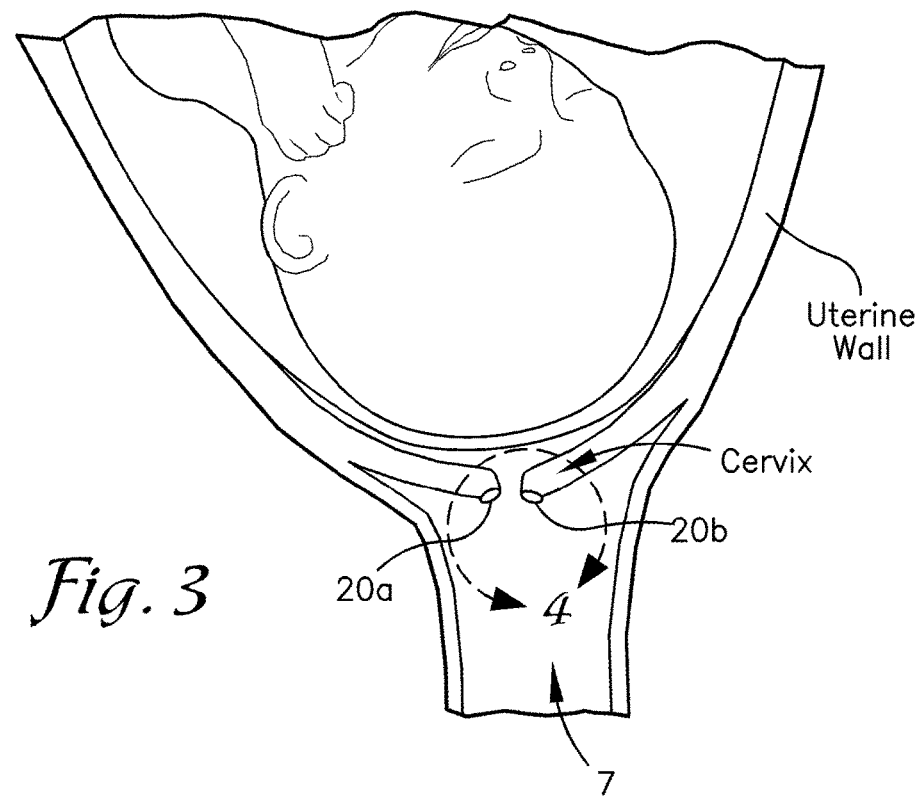
FIG. 3 is a partial side section detail of an exemplary female uterus with child and cervix showing placement of the microelectromechanical sensors in accordance with an embodiment of the system depicted in FIG. 2.
Figure 4:
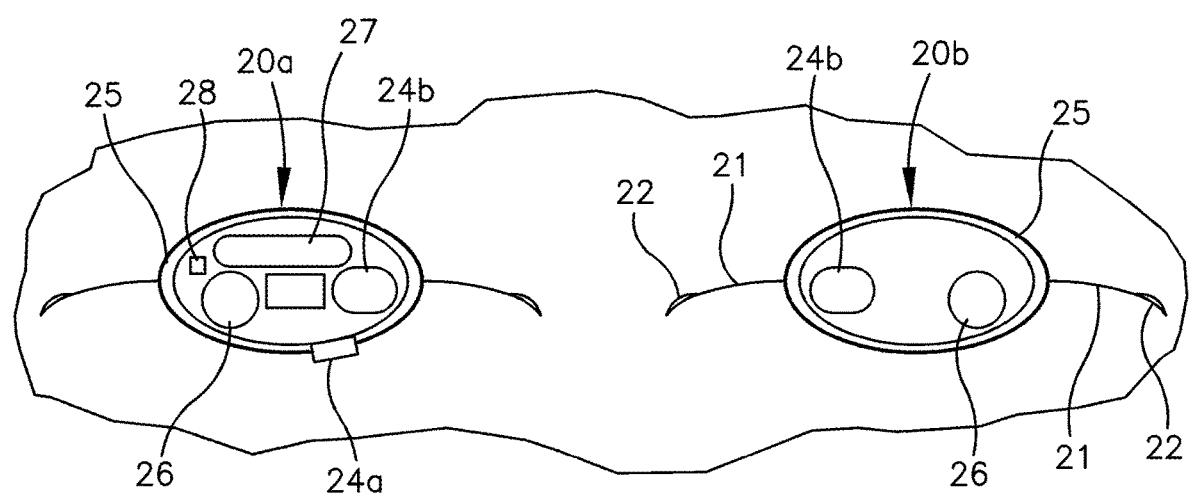
FIG. 4 is a bottom view taken along section 4 of FIG. 3 illustrating a portion of the exemplary cervix from FIG. 3 and showing exemplary placement of the microelectromechanical sensors in accordance with an embodiment of the system depicted in FIG. 3.

FIG. 3 illustrates a normal pregnancy with the cervical MEMS devices 20a and 20b being spaced generally symmetrically along the cervix view with the ferns positioned in a head-down orientation. FIG. 4 is a close-up view taken along the line 4 of FIG. 3 and illustrates a close-up view of a first and second cervical MEMS devices 20a, 20b which are exemplary embodiments of the cervical MEMS device 20 previously described.

Each first and second cervical MEMS devices 20a, 20b is generally elliptical and includes a laterally extending suture 21 terminating at a tip 22. The illustrated tip 22 is generally concave for sensing the surrounding conditions. Each cervical MEMS device 20 includes an outer biocompatible coating 25 and a variety of sensory elements 24a-b for sensing uterine, vaginal and cervix Characteristics; fluids and gasses. By way of illustration, the first cervical MEMS device 20a further includes a proximity sensor 24b, a pH sensor 24a, a power supply 26 and a transmitter 27 to provide power necessary to operate the sensory elements 24a-b and the transmitter 27. By way of illustration, the second cervical MEMS device 20b includes proximity sensor 24b and power supply 26 to also provide the necessary power for the second cervical MEMS device 20*b*. The pH sensor 24*a* is illustrated externally mounted on the MEMS device 20.

The cervical MEMS device 20 is generally a small implantable device, typically having dimensions less than an inch wide or long and less than a quarter of an inch thick, so that it can be surgically implanted to the cervix of the patient without obstructing or harming any normal body functions. It will be based on Microelectromechanical technology that will detect cervical dilation by directly measuring the cervix and signaling the MEMS receiver when cervical dilation starts to occur. The cervical MEMS device 20 preferably includes a battery providing the power supply 26, powering the sensory elements 24*a-b* such as the externally mounted pH sensor 24*a* or the pair of proximity sensors 24*b*, a transmitter 27 which may be a short range RF transmitter or transceiver, and a MEMS processor 28 or controller or logic circuitry to detect and receive sensory data from the sensory elements 24*a-b*, or alternatively the MEMS cervical data and process and control operation of the plural MEMS sensory elements 24*a-b*.

In an exemplary embodiment, each of the cervical MEMS devices 20 (the first cervical MEMS device 20*a* and the second cervical MEMS device 20*b*) are surgically attached to the cervix at different locations such as a first cervix location and a second cervix location and include the MEMS sensory element 24*a-b* such as the proximity sensor 24*b* and power supply 26. However, in one embodiment, the second cervical MEMS device 20*b* includes the transmitter 27.

Initially, after installation on the cervix, the pair of cervical MEMS devices 20 may be in a power conservation, normal proximity detection mode in which the relative location of the cervical MEMS devices 20 is determined using the pair of proximity sensory elements 24*b* associated with each cervical MEMS device 20 and compared by the MEMS processor 25 to a last position using a preprogrammed time interval such as an hour. If the reading is the initial measurement, then the MEMS processor 28 may wait the initial time interval before obtaining another reading. Upon the determination that the relative location has changed a distance greater than a programmed threshold distance then the cervical MEMS devices 20 may switch to an active detection mode in which the interval time period may be increased and readings obtained more frequently. In one embodiment, the MEMS processor 28 processes received sensory data from the sensory elements 24*a-b* into MEMS cervical data and transmitting it to the networked computing device 11 for example along a narrow band, short range, normal status RF signal. Upon sensing movement greater than the threshold amount, the cervical MEMS device 20 may immediately transmits an alert or signal to the MEMS receiver 11 indicating that the cervical MEMS devices 20 are in movement which may indicate the patient is in labor. Additionally, upon sensing a pH level greater than a threshold pH level, the cervical MEMS device 20 may immediately transmit an alert or signal to the MEMS receiver 11 indicating that vaginal fluid may be present and that the patient is in labor.

Upon the receipt of previously programmed threshold sensory conditions, the cervical MEMS devices 20 may switch to an elevated detection mode and start obtaining measurements more frequently, such as every fifteen (15) minutes to the MEMS receiver 11. If the cervical MEMS device indicates that movement has slowed or that fluid is no longer present for a programmed interval period of time, the cervical MEMS device may return to non-elevated detection mode and provide a preconfigured signal to the MEMS receiver 11 indicating the return to non-elevated detection mode whereby power is conserved and normal proximity detection measurements are conducted.

Should the cervical MEMS devices 20 indicate greater movement or greater pH levels a secondary signal or alert may be transmitted to the MEMS receiver 11. This may indicate that there is an emergency or it may simply indicate a secondary condition which the remote network user may wish to be notified about.

During installation, the MEMS device 20 is sutured in place to the edge of the cervix with the tips 22 and suture 21 being threaded through the tissue of the cervix and then secured in place. Once installed, the tip 22 and any excess suture 21 is removed. During pregnancy, the dilation of the cervix extends laterally and the distance separating the MEMS devices 20 become greater as the MEMS devices 20*a-b* are spaced laterally from each other. As the distance between the MEMS devices 20*a-b* increases, the proximity sensor 24*b* detects the changed position, converting the increased distance into an electrical signal which represents a distance which is then transmitted to the processor 28 as sensory data. The processor 28 then compares the changed position reading to a prior position reading or an initial position reading, and using previously configured parameters calculates a separation distance which is then transformed into MEMS cervical data which is available for selective transmission to the MEMS receiver 11.

The MEMS receiver 11 may include a display 11*d* which is adapted for graphically presented cervical status data 23 which is processed by the controller 11*c* from MEMS cervical data received from the transmitter 27 of the cervical MEMS device 20. The display 11*d* may graphically present cervical status data 23 to notify a user viewing the display 11*d* of the current and historical conditions of the cervix including the amount of dilation, the presence of vaginal fluid and other conditions which sensory elements 24*a-b* are measuring. During the normal mode, the display 11*d* may provide a graphical representation upon request of the measured conditions. During the elevated mode, the MEMS receiver 11 may provide an audible alert along with an elevated graphical representation to indicate the elevated mode.

Figure 5:
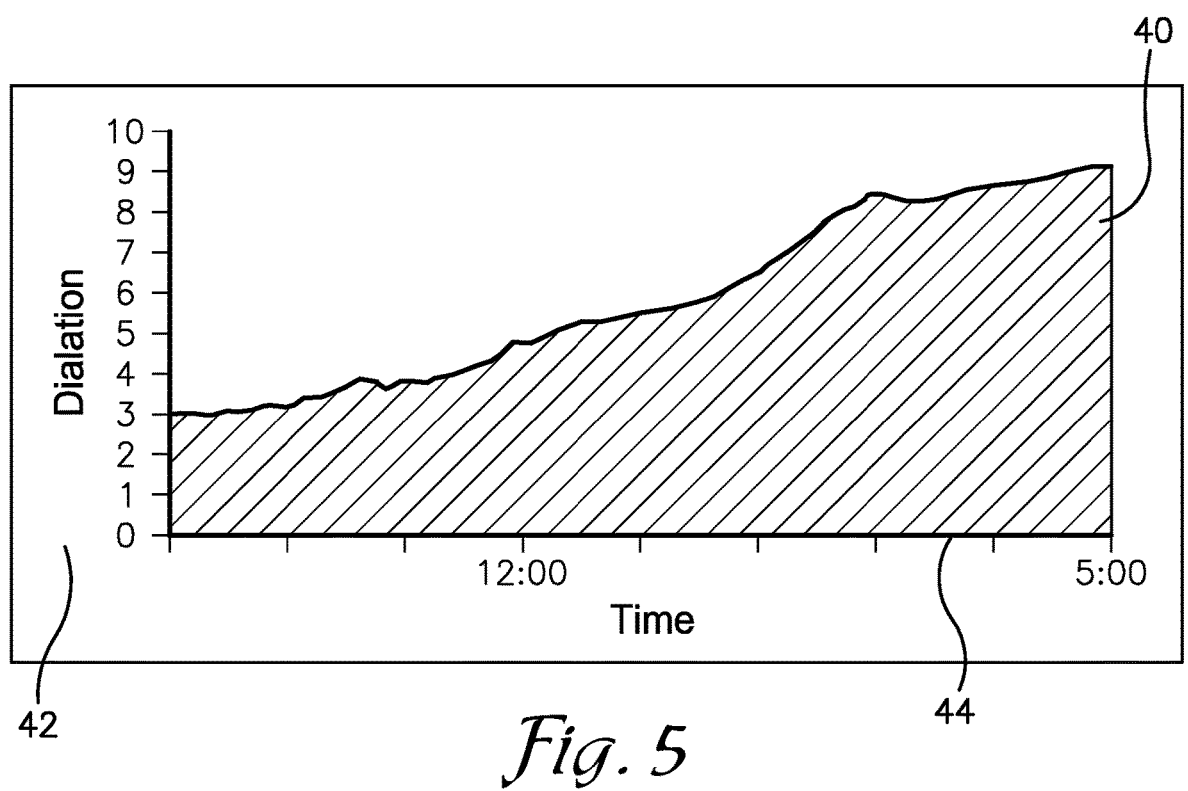
FIG. 5 is a graphical representation showing cervical dilation over time of an exemplary labor event associated with data received from the microelectromechanical sensors associated with a single patient during labor, the graphical representation optionally displayed on a computer screen in accordance with an aspect of the present invention.

FIG. 5 shows one embodiment of a display 11*d* presented by the cervical dilation application 18 on the MEMS receiver 11 which may be of benefit for a healthcare giver of compiled cervical status data. The graph illustrated in FIG. 5 shows a sample graph 40 plotting dilation 42 in centimeters (y axis) over time 44 (x axis) presenting a dilation record for a sample patient. The sample graph may be presented on the display 11*d* or it may be presented to a remote user on a remotely located network monitor device 14 connected via the remote network. In one example, the remotely located network monitor device 14 may be associated with a medical provider's office for remote monitoring of a plurality of office patients.

FIG. 5 shows one embodiment of a display 11*d* presented by the cervical dilation application on the MEMS receiver 11 which may be of benefit for a healthcare giver of compiled cervical status data. The graph illustrated in FIG. 5 shows a sample graph 40 plotting dilation 42 in centimeters (y axis) over time 44 (x axis) presenting a dilation record for a sample patient. This graphical display may be presented on display 11*d* or it may be presented to a remote user on a remotely located network monitor device 14 connected via the remote network monitor 16. In one example, the remotely located network monitor device 14 may be associated with a medical provider's office for remote monitoring of a plurality of office patients.

Figures 6, 7:
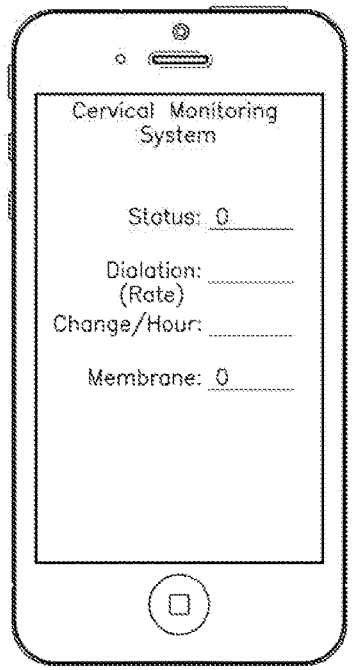
FIG. 6 is a exemplary embodiment of the remote monitoring device showing medical data transmitted to the remote device by the remote microelectromechanical labor notification system using data received from the microelectromechanical sensors in accordance with an aspect of the present invention.
FIG. 7 is a graphical representation showing cervical dilation data transmitted from a plurality of microelectromechanical sensors in communication with the computer for monitoring and displaying multiple patient's labor condition and status on a single graphical display of a computer screen in accordance with an aspect of the present invention.

FIG. 6 illustrates an alternative embodiment of the display 11d on an exemplary MEMS receiver 11 with numerical data representing the cervical status data 23 using the cervical dilation application 18. As illustrated in FIG. 6, the cervical status data 23 may include, but is not limited to typical labor health conditions such as: status (labor, non-labor), dilation and dilation rate (as a change per hour) and membrane condition (such as ruptured or normal). This information may by presented locally on the MEMS receiver 11 or it may be presented to a remote user on a remotely located network monitor device 14 connected via the remote network. As illustrated in FIG. 7, a plurality of cervical status data 23 may be presented for a plurality of patients, with each row on the exemplary table representing an individual patient associated with each of the received cervical status data 23 the cervical status data 23 including a unique patient identifier so that it can be designated separately from the other received cervical status data 23. The cervical status data 23 may also include a unique healthcare provider identifier so that the patients associated with a specific healthcare provider may be grouped together.

It is to be understood that while certain forms of the present invention have been illustrated and described herein, it is not to be limited to the specific forms or arrangement of parts described and shown.

What is claimed and desired to be secured by Letters Patent:

1. A system for labor detection by monitoring an internal status of a cervix for a labor condition said system comprising;
    a MEMS receiver comprising a processor, a controller, a short range wireless receiver and a long range wireless transceiver;
    said controller coupled to said processor, said short range wireless receiver and said long range wireless transceiver;
    said controller configured to control said MEMS receiver and said processor, such that MEMS cervical data is received by said MEMS receiver and processed by said processor into cervical status data, whereby said MEMS cervical data includes pH data and proximity data;
    said MEMS receiver configured to receive said MEMS cervical data at a timed interval;
    said MEMS receiver configured to process said MEMS cervical data into said cervical status data for transmission to a remote network monitor;
    wherein said cervical status data includes membrane condition;
    a first cervical MEMS device configured for implanting at a first cervix location and comprising a transmitter, a MEMS processor, a memory, a first power supply coupled to a first proximity sensor and a pH sensor; and
    a second cervical MEMS device configured for implanting at a second cervix location which is spaced from said first cervical MEMS device a distance;
    said second cervical MEMS device in communication with said first cervical MEMS device and comprising a second power supply coupled to a second proximity sensor;
    said second cervical MEMS device separated from said first cervical MEMS device said distance, wherein the MEMS processor is configured to process information representing the distance from said first proximity sensor and said second proximity sensor at the timed interval, wherein the proximity data includes the information representing the distance;
    wherein said first proximity sensor, second proximity sensor, and pH sensor provide said MEMS cervical data for selective transmission by said transmitter to said short range wireless receiver at said timed interval to said MEMS receiver;
    wherein said MEMS processor is configured to compare a relative change in information representing a prior distance of a previous instance stored in the memory to said information representing the distance with a predetermined threshold;
    wherein said first cervical MEMS device and second cervical MEMS device are configured to initially be in a normal proximity detection mode, and wherein upon the MEMS processor detecting that the relative change meets the predetermined threshold, the first MEMS device and the second MEMS device are switched to an active detection mode, and the transmitter is configured to transmit an alert to said MEMS receiver; and
    wherein in the active detection mode, said MEMS processor is configured to obtain said cervical data at an increased frequency, and wherein said transmitter transmits said MEMS cervical data to said MEMS receiver at said increased frequency.

2. The system for labor detection of claim 1 wherein said first cervical MEMS device and said second cervical MEMS device each include a biocompatible housing.

3. The system for labor detection of claim 1 wherein said MEMS cervical data including distance data calculated by said MEMS processor between said first and said second proximity sensors wherein said distance data indicates the labor condition.

4. The system for labor detection of claim 1 wherein said MEMS receiver further comprises a display for displaying cervical status data for monitoring the cervix for labor.

5. The system for labor detection according to claim 1 wherein said cervical status data further includes at least one of the following: labor status, dilation, and dilation rate.

6. A method of detecting labor comprising the steps of:
    providing a system for labor detection;
    wherein the system includes:
        a MEMS receiver comprising a processor, a controller, a short range wireless receiver and a long range wireless transceiver;
        said controller coupled to said processor, said short range wireless receiver and said long range wireless transceiver;
        said controller configured to control said MEMS receiver and said processor, such that MEMS cervical data is received by said MEMS receiver and processed by said processor into cervical status data, whereby said MEMS cervical data includes pH data and proximity data;
        said MEMS receiver configured to receive said MEMS cervical data at a timed interval;
        said MEMS receiver configured to process said MEMS cervical data into said cervical status data for transmission to a remote network monitor;
        wherein said cervical status data includes membrane condition;
        a first cervical MEMS device configured for implanting at a first cervix location and comprising a transmitter, a MEMS processor, a memory, a first power supply coupled to a first proximity sensor and a pH sensor; and a second cervical MEMS device configured for implanting at a second cervix location which is spaced from said first cervical MEMS device a distance;

said second cervical MEMS device in communication with said first cervical MEMS device and comprising a second power supply coupled to a second proximity sensor;

said second cervical MEMS device separated from said first cervical MEMS device said distance, wherein the MEMS processor is configured to process information representing the distance from said first proximity sensor and said second proximity sensor at the timed interval, wherein the proximity data includes the information representing the distance;

wherein said first proximity sensor, second proximity sensor, and pH sensor provide said MEMS cervical data for selective transmission by said transmitter to said short range wireless receiver at said timed interval to said MEMS receiver;

wherein said MEMS processor is configured to compare a relative change in information representing a prior distance of a previous instance stored in the memory to said information representing the distance with a predetermined threshold;

wherein said first cervical MEMS device and second cervical MEMS device are configured to initially be in a normal proximity detection mode, and wherein upon the MEMS processor detecting that the relative change meets the predetermined threshold, the first MEMS device and the second MEMS device are switched to an active detection mode, and the transmitter is configured to transmit an alert to said MEMS receiver; and wherein in the active detection mode, said MEMS processor is configured to obtain said cervical data at an increased frequency, and wherein said transmitter transmits said MEMS cervical data to said MEMS receiver at said increased frequency;

configuring the first cervical MEMS device for implanting at the first cervix location;

configuring the second cervical MEMS device for implanting at the second cervix location;

spacing said first cervical MEMS device an initial distance from said second cervical MEMS device and implanting the first cervical MEMS device and the second cervical MEMS device at the initial distance;

processing information representing the distance between the first and second proximity sensors at the timed interval;

receiving the cervical data at the MEMS receiver at the timed interval;

processing the cervical data into MEMS cervical status data by the processor of the MEMS receiver;

transmitting said MEMS cervical status data to the remote network monitor;

determining cervical status based upon the MEMS cervical status data;

transmitting said MEMS cervical data by said MEMS processor to said MEMS receiver; and graphically presenting said cervical status data on a display of said MEMS receiver.

7. A system for labor detection by monitoring for an active labor condition said system comprising;

a MEMS receiver in wireless communication with at least one elliptical MEMS device;

said MEMS receiver comprising non-transitory storage media, a processor, a graphical display, a receiver and a transceiver, said MEMS receiver configured to receive MEMS cervical data at a timed interval;

said processor of the MEMS receiver configured to process said MEMS cervical data into cervical status data;

a first elliptical MEMS device configured for implanting at a first cervix location and comprising a transmitter, a MEMS processor, a memory, and a first power supply coupled to a first proximity sensor;

a second elliptical MEMS device configured for implanting at a second cervix location in communication with said first elliptical MEMS device and comprising a second power supply coupled to a second proximity sensor;

said second elliptical MEMS device spaced at least a distance from said first elliptical MEMS device;

wherein the MEMS processor is configured to process information representing the distance from said first proximity sensor and said second proximity sensor at the timed interval;

wherein said MEMS processor is configured to compare a relative change in information representing a prior distance of a previous instance stored in the memory to said information representing the distance with a predetermined threshold;

wherein said first elliptical MEMS device and second elliptical MEMS device are configured to initially be in a normal proximity detection mode, and wherein upon the MEMS processor detecting that the relative change meets the predetermined threshold, the first elliptical MEMS device and the second elliptical MEMS device are switched to an active detection mode, and the transmitter is configured to transmit an alert to said MEMS receiver; and wherein in the active detection mode, said MEMS processor is configured to obtain said cervical data at an increased frequency, and wherein said transmitter transmits said MEMS cervical data to said MEMS receiver at said increased frequency.

8. The system according to claim 7 wherein at least one of said first elliptical MEMS device and said second elliptical MEMS device includes a pH sensor.

9. The system according to claim 7 wherein said timed interval is a preprogrammed time interval.

* * * * *